BEGONIA PLANT
Filed Jan. 27, 1972 2 Sheets-Sheet 2
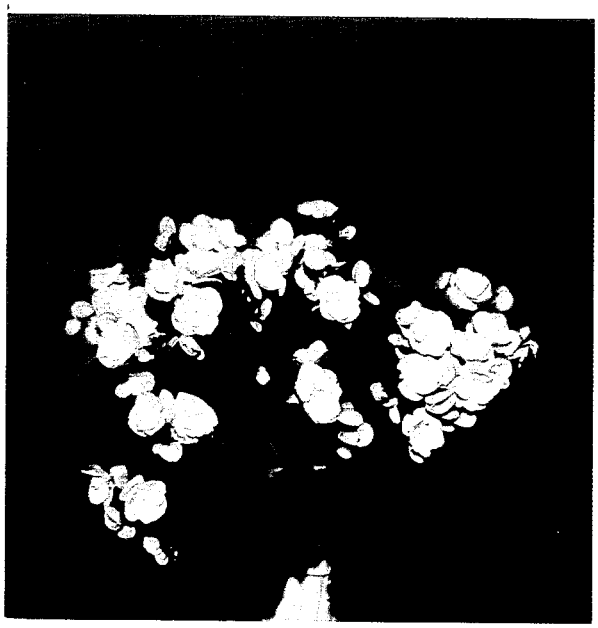
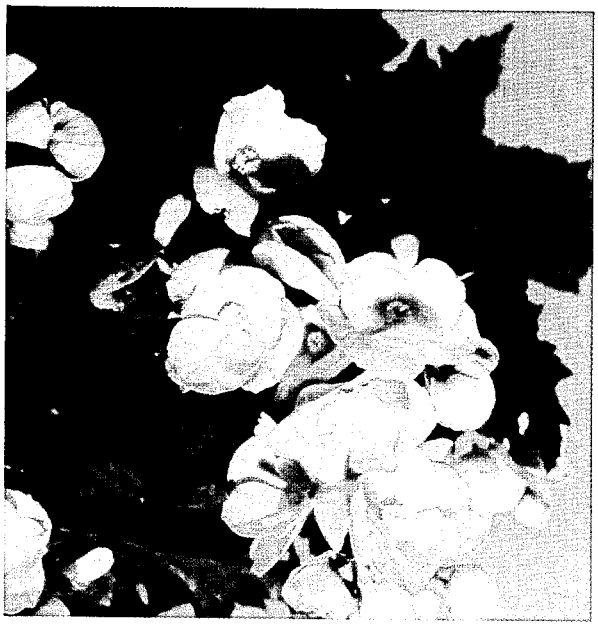

June 26, 1973 O. RIEGER Plant Pat. 3,365
BEGONIA PLANT
Filed Jan. 27, 1972 2 Sheets-Sheet 1
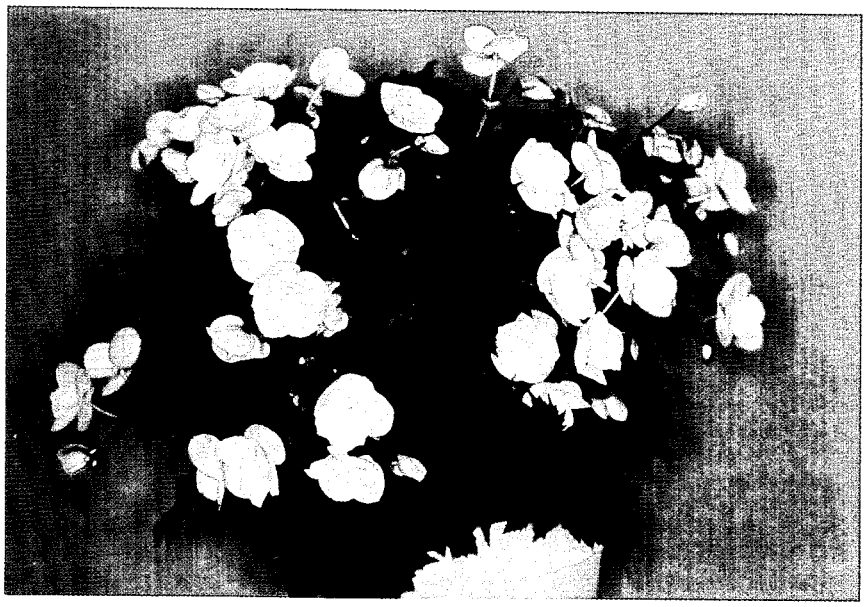
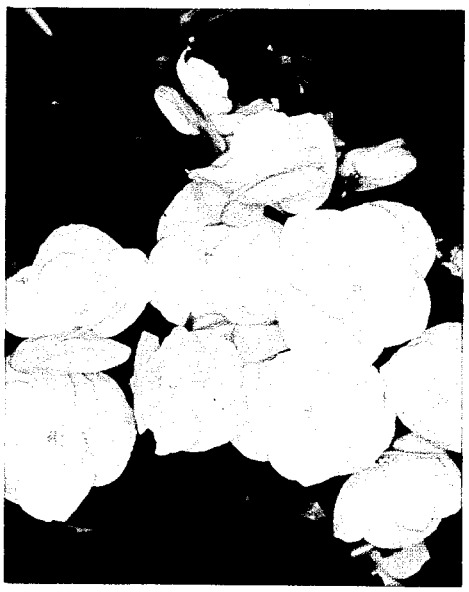

United States Patent Office

Plant Pat. 3,365
Patented June 26, 1973

3,365
BEGONIA PLANT

Otto Rieger, deceased, by Gertrud Rieger, legal representative, Nurtingen, Germany, assignor to Mikkelsens, Inc., Ashtabula, Ohio Filed Jan. 27, 1972, Ser. No. 221,456
Int. Cl. A01h 5/00
U.S. Cl. Plt.—68 1 Claim The present invention relates to a new and distinctive variety of begonia plant, botanically know as begonia elatior, discovered by me as a sport of the unpatented variety known as Rieger's Goldlachs.

The new variety was discovered in a nursery in Funfhausen, Germany, as a mutation in the form of several side branches of a plant of the parent variety in a flowering crop. Asexual reproduction of the new variety by continuous and line progressive leaf cuttings in Nurtingen, Germany, has established the new variety through successive propagations.

The new variety is disctinguished from the parent variety by the following characteristics:

(1) More compact plant habit.

(2) Better clarity in flower color.

(3) Approximately double the average number of petals.

(4) A distinctive, strongly indented foliage with serrated edges.

(5) Prolific production of underground adventitious shoots when propagated from leaf cuttings.

(6) Close internodes which result in a great number of leaves that give the finished plant a unique, full appearance, with the high leaf production being highly advantageous from a propagation standpoint where asexual reproduction is from leaf cuttings.

(7) An orange-red flower color, and full flowering form.

(8) The doubleness of the flowers enhances the appearance of the individual flowers and the overall plant.

It should be noted that certain of the above distinguishing characteristics when compared with the parent variety apply as well to present commercial begonia varieties. The new variety is particularly characterized by the relatively great production of adventitious shoots per cutting, thereby developing a much more dense and compact plant habit, with superior leaf production. The new variety is also unique by virtue of its strongly indented foliage with serrated or saw toothed edges.

In the accompanying photographic drawing, the photograph at the top of the sheet illustrates the entire plant, and the protograph at the bottom of the sheet is an enlarged view of the foliage and blooms.

The following detailed description of the new begonia variety is based on observations of the new variety grown in Nurtingen, Germany, and Ashtabula, Ohio. Color references are to the Royal Horticultural Society Color Chart.

Plant:

*Form.*—Bush, with abundant branching and compact habit; close internodes.

*Growth habit.*—Comparatively slow growing, but with superior sub surface adventitious shoot development.

*Rooting habit.*—Comparatively slow rooting habit.

*Blooming habit.*—Easy, full flowering habit with well dispersed flower cluster; may flower for upwards of six months. Flowering will usually cease under high temperatures and low light conditions.

*Blooming season.*—Natural season of November and December; by using leaf cuttings to produce vegetative shoots, and by controlling temperatures and daylength the new variety can be flowered at any time of the year.

Flower:

*Borne.*—Several to stem, in regular clusters, on medium length, strong stems.

*Bud.*—Flat, expanding to approximately ¾" in diameter before opening.

*Form.*—Double.

*Size.*—Comparatively small, averaging approximately 1½" in diameter.

*Petals.*—Number—6–8, under normal conditions 8; texture—smooth; appearance—inside, bright but not glossy; outside, dull, with coloring being several shades less than inside; shape—rounded; arrangement — alternate; color — orange-red #30B/C; some flecking at base of petals, color #28B; permanence—keeping qualities above average.

Reproductive organs:

*Stamens.*—Color approximately yellow-orange 15A/B.

*Pollen.*—Color approximately yellow-orange 14B/C.

*Styles.*—None seen to be able to describe.

*Ovaries.*—None seen to be able to describe.

Foliage:

*Size.*—Medium.

*Quantity.*—Very abundant.

*Shape.*—Highly serrated with saw toother edges, with shape and appearance being similar to maple leaf.

*Texture.*—Upper side leathery and velvety; underside glossy.

*Leaf petiole.*—Borne at sharp angle to main stem, blade at about 45°.

*Color.*—New foliage—upper side varies from green #138A to #137C; underside yellow green #147B/C; old foliage—upper side varies from yellow green #147A to #137A; underside varies from yellow green #146B to #137C.

*Disease resistance.*—Relatively resistant to botrytis and mildew, as compared with susceptible varities under commercial production practices.

I claim:

1. A new and distinct variety of begonia characterized particularly as to uniqueness by its distinctive, strongly indented foliage with serrated edges, prolific production of underground adventitious shoots when propagated from leaf cuttings, its abundance of leaves which give the finished plant a compact, full appearance; its abundance of petals and by its orange-red flower color with good clarity, and doubleness and full flower form.

No references cited.

ROBERT E. BAGWILL, Primary Examiner